United States Patent
Mori et al.

(10) Patent No.: US 6,239,177 B1
(45) Date of Patent: May 29, 2001

(54) TRANILAST-CONTAINING PREPARATION FOR EXTERNAL APPLICATION AND METHOD OF PRODUCING THE SAME

(75) Inventors: Masao Mori, Toyama; Noriyasu Saito, Shiojiri, both of (JP)

(73) Assignees: Lead Chemical Co., Ltd., Toyama-ken; Kissei Pharmaceutical Co., Ltd., Nagano-ken, both of (JP)

( * ) Notice: Subject to any disclaimer, the term of this patent is extended or adjusted under 35 U.S.C. 154(b) by 0 days.

(21) Appl. No.: 09/117,658

(22) PCT Filed: Feb. 6, 1997

(86) PCT No.: PCT/JP97/00283

§ 371 Date: Aug. 4, 1998

§ 102(e) Date: Aug. 4, 1998

(87) PCT Pub. No.: WO97/28793

PCT Pub. Date: Aug. 14, 1997

(30) Foreign Application Priority Data

Feb. 7, 1996 (JP) ..................................... 8-045493

(51) Int. Cl.$^7$ ......................... A61K 31/195; A61K 31/19
(52) U.S. Cl. ............................. 514/563; 514/568
(58) Field of Search ................... 424/443, 449, 424/448; 514/34, 772.6, 563, 568, 569

(56) References Cited

U.S. PATENT DOCUMENTS

| | | | |
|---|---|---|---|
| 4,978,531 | * 12/1990 | Yamazaki et al. | 424/448 |
| 4,990,340 | * 2/1991 | Hidaka et al. | 424/449 |
| 5,124,317 | * 6/1992 | Gatti et al. | 514/34 |
| 5,446,070 | * 8/1995 | Mantelle | 514/772.6 |
| 5,478,568 | * 12/1995 | Takayasu et al. | 424/449 |
| 5,656,286 | * 8/1997 | Miranda et al. | 424/449 |
| 5,719,197 | * 2/1998 | Kanios et al. | 514/772.6 |
| 5,725,874 | * 3/1998 | Oda et al. | 424/443 |

FOREIGN PATENT DOCUMENTS

| | | | |
|---|---|---|---|
| 0709099 A2 | 1/1996 | (EP) | . |
| 813879 | * 12/1997 | (EP) | A61F/13/00 |

OTHER PUBLICATIONS

CA, XP–002079138, Abstract no. 63951 & JP63238024 A2., 1988.
Database WPI, 91–143149, XP–002079139, abstract & JP 03077820. 1991.
Database WPI, 93–239979, XP–002079140, abstract & JP 05163222. 1993.

* cited by examiner

Primary Examiner—William R. A. Jarvis
Assistant Examiner—Vickie Kim
(74) Attorney, Agent, or Firm—Nath & Associates PLLC; Gary M. Nath; Harold L. Novick

(57) ABSTRACT

An external preparation containing tranilast which is excellent in the release of the active ingredient contained therein, achieves a high percutaneous absorption, fully ensures the effective drug concentration in the skin tissue and little irritates the skin This preparation is composed of an aqueous base containing as the active ingredient tranilast, its salt or a mixture thereof. The aqueous base contains a solubilizer for tranilast, a dispersant, an absorption aid, an adhesive and/or a shape retaining agent, and water. The active ingredient has been solubilized by the above-mentioned solubilizer and dispersed in the aqueous base by the above-mentioned dispersant.

8 Claims, 1 Drawing Sheet

TRANILAST-CONTAINING PREPARATION FOR EXTERNAL APPLICATION AND METHOD OF PRODUCING THE SAME

This application is 371 of PCT/JP97/00283 filed on Feb. 6. 1997.

FIELD OF THE INVENTION

The present invention relates to a preparation for external application containing tranilast as an active ingredient, more specifically to a preparation for topical application giving good transdermal absorbability of the active ingredient in the preparation due to improvement of the base and capable of sufficiently keeping an effective drug concentration in the skin tissue after application, which preparation is directed to treat keloid having little skin irritation, hypertrophic scar, psoriasis, palmoplantar pustulosis, prurigo nodularis including urticaria perstans, allergic dermatitis (e.g., atopic dermatitis, contact dermatitis, dutaneous pruritus, sting of an insect, priurigo simplex acuta, etc.), the other eczema and dermatitis including progressive palmoplantar keratoderma and lichen symplex chronicus.

BACKGROUND OF THE INVENTION

An antiallergic drug, tranilast, has been commercially available as a therapeutic agent for allergic diseases. It has also been reported to show excellent pharmaceutical effect on keloid and hypertrophic scar (Kiyoshi Ichikawa et al., Oyo Yakuri (Pharmacometrics) 43(5), 401 (1992), Haruo Suzawa et al., Nichi Yakuri-shi (Folio Pharmacol Japan) 99, 231 (1992)). Tranilast has been used in the dosage form for oral administration such as capsules, tablets, dry syrup, fine granules, and the like. However, the drug orally taken is absorbed from the digestive tract through portal vein to liver where the drug is metabolized to give a so-called first passing effect. Thereafter, a part of the drug is transferred to local sites and its biological availability is decreased. Accordingly, it is necessary to administer a relatively large amount of the drug so as to maintain the effective drug concentration in blood, which increases manifestation of side effects. Further, preparations for external application directly applied to local sites of skin, particularly patches, have been considered favorable for the treatment of keloids, hypertrophic scar, and allergic dermatitis so that it is necessary to maintain an effective drug dosage sufficiently in the skin.

Attention has been paid to patches as preparations for topical application as well as a new route for applying systemic drugs as transdermal drug delivery system (TDS). In other words, in TDS, a drug absorbed from its preparation through epidermis is taken into blood stream via subcutaneous capillary vessels while a portion of the drug is transferred directly to local skin tissues without being taken into blood stream. Aiming at such a topical application effect, a number of patches utilizing non-steroid anti-inflammatory drug systems (NSAIDS) have been already developed and commercially available.

Further, subcutaneous application by patches is effective as the controlled release method of drugs by which effects of drugs can be prolonged and the concentration of drugs in blood can be controlled. Thus, it is possible to suppress manifestation of side effects.

However, skin inherently has a property to defend the inside of body from foreign substances that may invade from the outside. Keratolytic agents such as Azone are sometimes used as a base in order to increase transdermal absorption of a drug. Such agents give high skin irritation and thus may possibly cause side effects such as an eruption on the skin. Transdermal absorbability depends on characteristics of the molecule, which extremely limits formulation of the drugs that can give effective transdermal absorption.

Tranilast is sparingly soluble in water. Among organic solvents, it is hardly soluble in methanol, ethanol, ethyl acetate, while it is soluble in dimethyl formamide, pyridine, dioxane, and acetone though these solvents are not suitable for the base of preparations for external application. The drug can be solved to some extent in a kind of fatty acid and its ester, animal and vegetable oils and fats, terpene compounds, and alcohols, but the solubility is not sufficient and the drug cannot be dispersed well in the preparations. This affects transdermal absorbability of tranilast and the solubility of the drug makes it difficult to formulate the drug into a patch.

As a preparation containing tranilast for external application, a patch containing tranilast has been developed, which contains a kind of fatty acid and alcohols as absorption aids to improve cutaneous absorbability (Japanese Patent Application Laid-Open No. Hei 4-99719). However, this patch requires a large amount of absorption aids, such as fatty acid ester or alcohols, which might possibly cause skin irritation.

A tranilast-containing ointment has also been developed, which contains a basic aqueous solution as an absorption aid (Japanese Patent Application Laid-Open No. Hei 6-128153). This preparation for external application has basic pH due to the basic aqueous solution contained as an absorption aid. The basic substance itself might possibly cause skin irritation. Thus, there are problems that make it difficult to put the preparations into practical use.

SUMMARY OF THE INVENTION

An object of the present invention is to solve the above described problems in the prior art to achieve the practical use of the preparation for external application containing tranilast as an active ingredient, which has good transdermal absorbability of the active ingredient in the preparation, sufficiently keeps a drug concentration effective in the skin tissues, and shows little skin irritation.

The earlier report (Toyomi Waseda, The Japanese Journal of Dermatology, 99 (11), 1159 (1989)) describes that the effective concentration of tranilast in the skin tissue for treatment of keloid patients is about 8 to 10 $\mu$g/g when it is orally administered in a dose of 300 mg/day in three divided doses for three days. Another earlier report (Yasuo Goto et al., Kiso to Rinsho (The Clinical Report), 25(15), 69 (1991)) discloses that in the experiment using rat carrageenan-induced granulation tissue model a dose-dependent inhibitory effect was observed when tranilast was orally administered in a dose of 50, 100, and 200 mg/kg for consecutive 14 days and the drug concentration in the skin tissue one hour after the final administration was 4.2±0.4, 10.3±0.9, and 23.17±1.7 $\mu$g/g, respectively. Consequently, the tranilast concentration in the skin tissue after its application to the skin should desirably be comparable to or higher than the values as described above.

Keloid, hypertrophic scar, and allergic dermatitis are diseases giving some appearance on the skin surface that is not only apparently ugly but also sometimes accompanied by strong itchiness or pain as subjective symptoms. Accordingly, it is preferable that preparations for external application to be directly applied to the diseased part should not produce irritation by contact and the base in the preparation does not cause skin irritation. Particularly, patches are preferably elastic and do not have undue strong adhesiveness so that little resistance occur when they are detached. In this connection, a cataplasm containing water or a soft type of plasters is desired.

The present invention provides a preparation for external application and a method of producing it to achieve the above object, which preparation contains an aqueous base comprising tranilast, its salt, or a mixture thereof as an active ingredient, in which the aqueous base comprises a dissolution medium, a dispersant, an absorption aid, an adhesive, and/or a form-keeping agent, and water, the active ingredient is dissolved in the dissolution medium, and dispersed in the aqueous base by means of the dispersant. The present invention provides such a preparation for external application comprising tranilast and a patch for external application which comprises a support having the preparation for external application coated thereon.

Further, the present invention relates to a method of producing a preparation for external application containing tranilast, which comprises dissolving an active ingredient selected from tranilast, its salt, or a mixture thereof in a dissolution medium, adding thereto a dispersant, and mixing the solution with an aqueous base comprising an absorption aid, an adhesive, and/or a form-keeping agent, and water, and to a method of producing a patch for external application which comprises coating the above preparation for external application on a support.

DETAILED DESCRIPTION OF THE INVENTION

Figure 1:
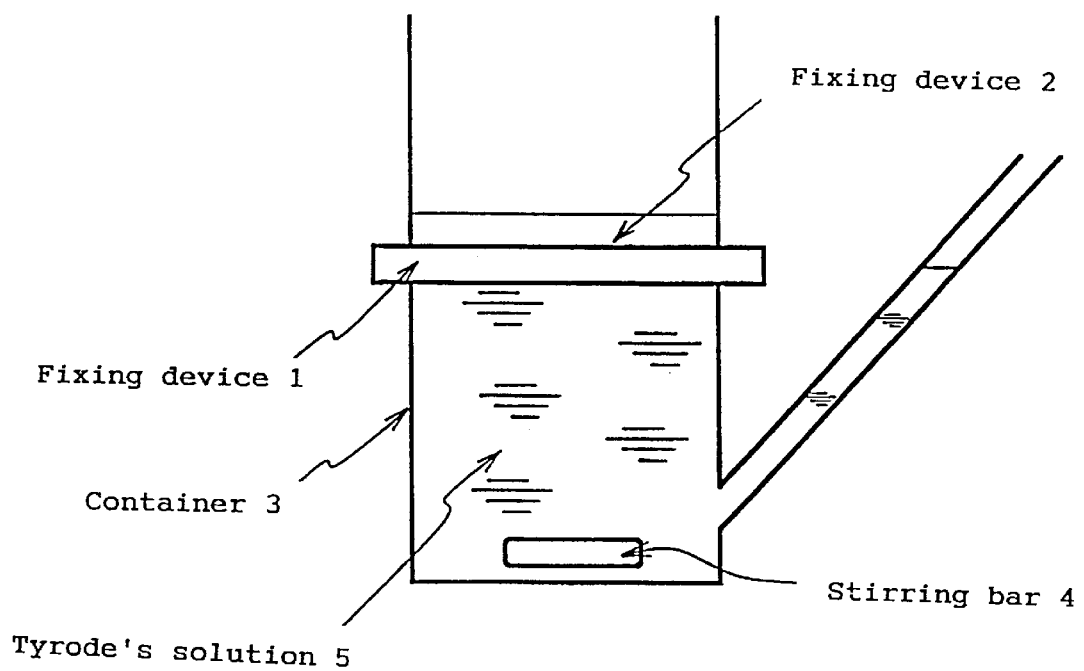
FIG. 1 shows a permeation/diffusion cell used in the test for skin permeation rate of the drug in the preparation of the present invention.

Tranilast, which is the active ingredient of the preparation for external application of the present invention, is N-(3,4-dimethoxycinnamoyl)-anthranilic acid represented by the following formula or salt thereof:

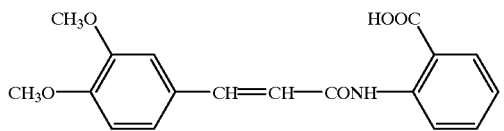

The content of tranilast in the preparation is preferably 0.05 to 5 wt %. If the content of the active ingredient is too low, its pharmacological effect is insufficient. If it is too high, it does not show additional merit and, thus, is economically disadvantageous.

In the preparation for external application of the present invention, the dissolution medium to solve tranilast therein is selected from oily substances including fatty acids and derivatives thereof, animal and vegetable oils and fats, terpene compounds, alcohols, crotamiton, N-methyl-2-pyrrolidone, and triethanolamine.

The fatty acids and derivatives thereof that can be used as the dissolution medium are monocarboxylic acids or esters thereof having 3 to 30 carbon atoms. The fatty acids include octadecanoic acid, oleic acid, and linoleic acid. The fatty acid esters include glycerol monocaprate, tetradecyl tetradecanoate, hexadecyl hexadecanoate, oleyl oleate, and isopropyl myristate. Further, fatty acid alkali metal salts are exemplified by fatty acid sodium salts.

The animal and vegetable oils and fats include almond oil, olive oil, camellia oil, persic oil, peppermint oil, soy bean oil, sesami oil, mink oil, cottenseed oil, corn oil, safflower oil, coconut oil, eucalyptus oil, castor bean oil, hydrogenated castor bean oil, soybean lecithin, and the like. The terpene compounds include menthol, menthone, limonene, pinene, piperidone, terpinene, terpinolene, terpinol, and carveol. The alcohols are non-aqueous alcohols, such as benzyl alcohol, and octanols.

Further, examples of organic solvents that can be used as the dissolution medium other than those described above include crotamiton, N-methyl-2-pyrrolidone, triethanolamine, and the like.

Among the above oily substances, preferable examples are oleic acid, linoleic acid, glycerol monocaprate, oleyl oleate, castor bean oil, hydrogenated castor bean oil, soybean oil, soybean lecithin, 1-menthol, menthone, limonene, benzyl alcohol, crotamiton, N-methyl-2-pyrrolidone, and triethanolamine. Particularly, crotamiton and N-methyl-2-pyrrolidone are most preferable because they do not only dissolve tranilast but also enhance its transdermal absorption. The dissolution medium may be used alone or in combination of two or more thereof. Its total content is preferably 2 to 5 wt %.

When a solution obtained by solving tranilast in the dissolution medium is mixed with the aqueous base comprising an absorption aid, an adhesive, and/or a form-keeping agent, and water upon production of the preparation for external application, tranilast must be uniformly dispersed in the final preparation. Since tranilast is extremely sparingly soluble in water as described above, it is not solved in part when mixed with the aqueous base and gives poor dispersibility. If the drug is not sufficiently dispersed in the preparation, its amount to be released is lowered, which results in a decrease in the amount transdermally absorbed.

According to the present invention, the preparation with good dispersibility can be produced by dissolving tranilast dissolved in the dissolution medium, adding the dispersion medium thereto, mixing the solution well to allow the dispersion medium to retain at least a part of, preferably substantially all amount of, tranilast, and kneading it with the aqueous base. The dispersion medium to be used is pharmaceutically acceptable solid powder, particularly inorganic solid powder, having ability to retain tranilast dissolved in the dissolution medium. Preferable examples of the dispersion medium are silicon dioxides such as silicon dioxide hydrate or soft silicic acid anhydride, and silicates such as magnesium silicate hydrate or aluminum silicate hydrate, with silicon dioxide hydrate (white carbon) being most preferred.

Namely, a preparation with good dispersibility can be prepared by dissolving tranilast in the dissolution medium, adding white carbon to the solution, mixing it thoroughly to allow tranilast to be adsorbed, and mixing the resulting dispersion with the aqueous base.

The ratio of the amount of the dispersion medium to the total amount of tranilast and the dissolution medium is ⅓ to ⅕.

The absorption aid for enhancing absorption of tranilast from the preparation into the skin tissue is selected from fatty acids and derivatives thereof that are used as a base in preparations for external application, animal and vegetable oils and fats, terpene compounds, alcohols, crotamiton, and N-methyl-2-pyrrolidone. Preferable examples thereof include oleic acid, 1-menthol, ethanol, propylene glycol, butanediol, 1,2,6-hexanetriol, benzyl alcohol, crotamiton, and N-methyl-2-pyrrolidone. These may be used alone or in combination of two or more thereof. Propylene glycol, butanediol, or N-methyl-2-pyrrolidone is most preferably used. These compounds can be added to the preparation in an amount of 0.5 to 10 wt %, preferably 2 to 5 wt %, to keep the sufficient drug concentration in the skin tissue after its application without causing skin irritation.

The pH value is another factor that enhances absorption of tranilast into the skin tissue. Tranilast is absorbed well into the skin at the pH range from the neutral region to the weak acidic region. Preferable pH range is 3.5 to 7.5 taking account of skin irritation of the preparation and form-keeping ability Citric acid and tartaric acid can be used to adjust the pH of the preparation.

The patch for external application is required not to cause contact irritation on the diseased part, to keep the form of the preparation, and to retain adhesiveness sufficiently, because the preparation is directly applied on the diseased part exposed on the skin surface. As the patch that satisfies the above requirements, aqueous types are preferably used though non-aqueous soft type plasters can also be used.

Water-soluble polymers to be used as the adhesives and/or the form-keeping agent includes polyacrylic acid and its derivatives, acrylate copolymer and its emulsion, cellulose derivative and its derivative, gum arabic, gelatin, casein, polyvinyl alcohol, polyethylene glycol, polyvinyl alcohol, polyethylene glycol, polyvinyl pyrrolidone, methyl vinyl ether/maleic anhydride copolymer and its emulsion, and naturally-occurring polysaccharides. These compounds may be used alone or in combination of two or more thereof. Its total amount to be added to the preparation ranges from 5 to 15 wt %. Preferably, polyacrylic acid and its derivatives, and acrylate copolymer and its emulsion are used. In the case of using sodium polyacrylate, it is possible to use as an aluminum compound capable of crosslinking activated alumina, synthetic aluminum silicate, aluminum hydroxide, and the like.

Examples of fat-soluble polymers that can be used as the adhesive and/or the form-keeping agent include natural rubber, isoprene rubber, polyisobutyrene rubber, styrene-butadiene rubber, styrene-isoprene-styrene block copolymer, styrene-butadiene-styrene block copolymer, silicone, rosin, polybutene, lanolin, petrolatum, plastibase, beeswax, and solid paraffin.

Polyhydric alcohols that can be used as the adhesive and/or the form-keeping agent include glycerol, polyethylene glycol, ethylene glycol, and D-sorbitol. These can be used alone or in combination of two or more thereof. The total amount to be added is preferably 5 to 40 wt %.

Using the above-described adhesive and/or form-keeping agent, it is possible to provide the tranilast-containing patch for external application that can keep adhesiveness, its form, and flexibility for a long time, with causing little skin irritation.

Further, if desired, it is possible to use a nonionic surface active agent or an inonic surface active agent, the other additives for medicines, for example, polyacrylic acid metal salt, bentonite, titanium oxide, and the like, in a necessary amount.

According to the present invention, the thus-prepared preparation for external application containing tranilast is spread on the support fabric such as flannel, nonwoven fabric, or the like and a film for peeling such as polyethylene, polypropylene, polyester, or the like on the exposed surface of the opposite side of the support fabric. The resulting products can be brought to market as a preparation for external application.

It is also possible to use the preparation for external application of the present invention as ointment or cream to be directly applied on the diseased part as it is without spreading on the support.

In the preparation for external application containing tranilast according to the present invention, tranilast, which is sparingly soluble in water, is dissolved in the dissolution medium and dispersed in the aqueous base with being retained by the dispersion medium. Thus, tranilast is uniformly dispersed in the aqueous base. Because of this, the active ingredient is easily released to provide high skin absorbability, its effective concentration in the skin tissue after its application is sufficiently maintained with little skin irritation.

DESCRIPTION OF PREFERRED EMBODIMENT

The following Examples will demonstrate the present invention in more detail, but are not construed to limit the scope of the present invention.

EXAMPLE 1

Three g of tranilast was dissolved in a mixed solution of 20 g of crotamiton and 10 g of ethanol by gradually heating to 60 to 70° C. After adding 7 g of white carbon thereto, the mixture was thoroughly mixed and ethanol was removed under reduced pressure. Then, 5 g of 1-menthol and 2.5 g of titanium oxide were added thereto and the mixture was mixed to prepare a tranilast solution. Separately, 25 g of tartaric acid was dissolved in 552 ml of water followed by adding 50 g of sodium polyacrylate, 60 g of polyacrylate starch, and 250 g of glycerol. The resulting mixture was mixed well to prepare an aqueous base mixture.

The tranilast solution, the aqueous base mixture, 0.5 g of dry aluminum hydroxide gel, and 25 g of methyl acrylate/ 2-ethylhexyl acrylate copolymer resin emulsion were uniformly kneaded to obtain 0.3% tranilast-containing preparation for external application. The pH of the preparation was 5.2.

EXAMPLE 2

Three g of tranilast was dissolved in a mixed solution of 20 g of crotamiton and 25 g of N-methyl-2-pyrrolidone and 10 g of ethanol. After adding 7 g of white carbon thereto and mixing the solution well, ethanol was removed under reduced pressure. Then, 5 g of 1-menthol and 2.5 g of titanium oxide were added and mixed to prepare a tranilast solution. Separately, 25 g of tartaric acid in 527 ml of water was mixed well with 50 g of sodium polyacrylate, 60 g of starch acrylate, and 250 g of glycerol to prepare an aqueous base mixture.

The tranilast solution, the aqueous base mixture, 0.5 g of dry aluminum hydroxide gel, and 25 g of methyl acrylate-2-ethylhexyl acrylate copolymer resin emulsion were kneaded uniformly to obtain 0.3% tranilast preparation for external application. The pH of the preparation was 5.2.

EXAMPLE 3

In the same composition containing tranilast and the base for external application as described in Example 1, 50 g of butanediol was added to the aqueous base mixture and glycerol was used in an amount of 200 g in place of 250 g to obtain 5% butanediol-containing tranilast preparation for external application.

EXAMPLE 4

In the same composition containing tranilast and the base for external application as described in Example 3, propylene glycol was used in place of butanediol to obtain 5% propylene glycol-containing tranilast preparation for external application.

EXAMPLE 5

In the same composition containing the base for external application as described in Example 1, 1% tranilast preparations for external application each having the pH of 4.3, 5.4, 6.3, and 7.4 were obtained using 10 g of tranilast, tartaric acid in an amount varied as shown in the following table, and various sodium polyacrylate (50 g) as shown in the following table.

|  | Tartaric acid (g) | Sodium polyacrylate (Showa Denko k.k) | pH |
| --- | --- | --- | --- |
| Example 5-1 | 50 | Viscomate NP-700 | 4.3 |
| Example 5-2 | 20 | Viscomate NP-700 | 5.4 |
| Example 5-3 | 10 | Viscomate NP-600 | 6.3 |
| Example 5-4 | 0 | Viscomate F480SS | 7.4 |

Performance Evaluation Test

TEST EXAMPLE 1

Using the preparations of Examples 5-1 through 5-4, influences of pH on penetrability of the drug into the skin was evaluated by the in vitro test with the penetration rate as an index.

In this test, penetration/diffusion cell shown in FIG. 1 was used.

The rat abdominal skin was interposed in the fixing device 1, a patch having the test preparation spread on the support was attached to the fixing device 2 so as to contact the preparation for external application with the rat abdominal skin on the fixing device 2. In order to prevent air from entering the container 3, 5.18 ml of Tyrode's solution was added thereto. The penetration/diffusion cell was placed in the incubator maintained at 37° C., Tyrode's solution 5 was stirred with the stirring bar 4 and a 0.5 ml portion of Tyrode's solution was sampled at each point of time within 1 to 7 hours. The drug concentration in the sampled solution was measured to calculate the penetration rate of the drug in the test preparation for external application into the rat abdominal skin. The drug concentration was measured by HPLC. The results are shown in Table 1.

Conditions for HPLC

| Column: | CAPCELLPAK C18 (SG120), 4.6 mm × 150 mm |
| --- | --- |
| Mobile phase: | 50 mM ammonium acetate buffer (pH 6.0)/ acetonitrile |
| | = 750/250 (0 to 10.5 min) |
| | → 375/625 (10.5 to 15 min) |
| | → 750/250 (15 to 20 min) |
| Column temperature: | 40° C. |
| Flow rate: | 1.0 ml/min |
| Detection wavelength: | 320 nm for tranilast |
| | 254 nm for internal standard substance (ethyl p-hydroxybenzoate) |
| Retention time: | 5 min for tranilast, |
| | 10 min for internal standard substance |

TABLE 1

Influences of pH on transdermal absorption of the preparation for external application

| | Amount penetrated ($\mu$g/cm$^2$) n = 3 | | | | | Penetration rate*[1] |
| --- | --- | --- | --- | --- | --- | --- |
| pH of Base | 1 hr | 3 hr | 5 hr | 7 hr | 24 hr | (5 to 24 hr) |
| 4.3 | 0.00 | 0.02 | 0.15 | 0.40 | 4.21 | 0.22 ± 0.02 |
| 5.4 | 0.00 | 0.03 | 0.10 | 0.40 | 3.79 | 0.20 ± 0.03 |
| 6.3 | 0.00 | 0.00 | 0.12 | 0.35 | 2.93 | 0.15 ± 0.03 |
| 7.4 | 0.00 | 0.00 | 0.04 | 0.11 | 0.17 | 0.06 ± 0.02 |

*[1] $\mu$g/cm$^2$/hr S.E.

TEST EXAMPLE 2

In the same manner as in Examples 3 and 4, the preparations were prepared so as to make each of the amount of the absorption aid, propylene glycol and butanediol, 2%, 5%, and and 10% and make the amount of N-methyl-2-pyrrolidone 2.5%. The resulting preparations were respectively spread on the support to give patches. Using the resulting patches, skin absorbability of the skin absorption aids, that is, propylene glycol, butanediol, and N-methyl-2-pyrrolidone, was evaluated by measuring the penetration rate of tranilast and the amount of tranilast accumulated in the skin. The results are shown in Table 2. The skin penetration rate was determined in accordance with the method as described in Test Example 1. The drug concentration in the skin was determined as described below.

Abdominal body hair of Wistar-Imamichi male rats (200 g) was cut with a hair clipper or a shaver under anesthesia with ether and the preparation was applied to the abdominals skin (3×3 cm). Eight hours after application of the preparation, the rats were sacrificed and the stratum corneum was removed thoroughly, by stripping with cellophane adhesive tape on the skin at the middle of the part where the preparation was applied. After removing fat, capillary vessels, and the like in dermis, a part of the dermis was taken out by punching with a puncher($\phi$1.0 cm) and cut into thin strips. Then, the thin strips of the skin section were mixed with 2 ml of methanol, 1 ml of an ethanol solution of ethyl p-hydroxybenzoate (internal standard substance) (10 $\mu$g/ml), and 0.5 ml of 50 mM ammonium acetate buffer (pH 6.0). The resulting mixture was homogenized well by micro-homogenization and centrifuged at 15,000 rpm for 5 min. The resulting supernatant was applied to HPLC. The same conditions for HPLC as in Test Example 1 were followed.

TABLE 2

Effect of skin absorption aid on transdermal absorption of tranilast

| Absorption aid | Penetration rate ($\mu$g/cm$^2$/h) | Drug concentration in skin ($\mu$g/g) |
| --- | --- | --- |
| — | 0.22 ± 0.01 | 26.01 ± 1.29 |
| 2% propylene glycol | 0.38 ± 0.07 | 44.93 ± 4.66 |
| 5% propylene glycol | 0.33 ± 0.07 | 45.92 ± 8.71 |
| 10% propylene glycol | 0.68 ± 0.10 | 35.24 ± 0.69 |
| 2% butanediol | 0.50 ± 0.13 | 36.04 ± 5.08 |
| 5% butanediol | 0.64 ± 0.18 | 49.74 ± 7.19 |
| 10% butanediol | 0.83 ± 0.07 | 33.08 ± 0.92 |
| 2.5% N-methyl-2-pyrrolidone | 0.68 ± 0.10 | 53.23 ± 10.88 |

What is claimed is:

1. A preparation for external application containing an aqueous base comprising tranilast, its salt, or a mixture thereof as an active ingredient, the preparation for external application containing tranilast characterized in that said aqueous base comprises a dissolution medium selected from the group consisting of crotamiton and N-methyl-2-pyrrolidone to dissolve tranilast, a dispersant selected from silicon dioxides or silicates, an absorption aid, and an adhesive, and/or a form-keeping agent, and water, and the active ingredient is dissolved in said dissolution medium, and is supported on said dispersant and dispersed in the aqueous base by means of said dispersant.

2. A preparation for external application containing tranilast as claimed in claim 1, wherein the absorption aid is propylene glycol or butanediol.

3. A preparation for external application containing tranilast as claimed in claim 1, wherein the adhesive and/or form-keeping agent is selected from the group consisting of water-soluble polymers, fat-soluble polymers and polyhydric alcohols.

4. A preparation for external application containing tranilast as claimed in claim 1, characterized in that pH value of a preparation ranges 3.5 to 7.5.

5. A patch for external application, wherein a preparation for external application containing tranilast as claimed in claim 1 is coated on a support.

6. A preparation for external application as claimed in claim 1 wherein the preparation for external application is ointment or cream.

7. A method of producing a preparation for external application containing tranilast, characterized by dissolving an active ingredient selected from the group consisting of tranilast, its salt and a mixture thereof in a dissolution medium selected from crotamiton and N-methyl-2-pyrrolidone, then, mixing the resultant solution with a dispersant selected from silicon dioxides or silicates to support the active ingredient on the dispersant, and kneading the resultant mixture with an aqueous base comprising an absorption aid, and an adhesive, and/or a form-keeping agent, and water.

8. A method of producing a patch for external application containing tranilast, characterized by dissolving an active ingredient selected from the group consisting of tranilast, its salt, and a mixture thereof in a dissolution medium selected from the group consisting of crotamiton and N-methyl-2-pyrrolidone, then, mixing the resultant solution with a dispersant selected from silicon dioxides or silicates to support the active ingredient on the dispersant, and kneading the resultant mixture with an aqueous base comprising an absorption aid, and an adhesive, and/or a form-keeping agent, and water, and coating the resultant preparation on a support.

* * * * *